United States Patent [19]

Althuis

[11] 4,011,324
[45] Mar. 8, 1977

[54] ESTERS AND AMIDES OF PYRIMIDO[4,5-b]QUINOLIN-4(3H)-ONE-2-CARBOXYLIC ACIDS AS ANTIULCER AGENTS

[75] Inventor: Thomas H. Althuis, Groton, Conn.

[73] Assignee: Pfizer Inc., New York, N.Y.

[22] Filed: Jan. 20, 1976

[21] Appl. No.: 650,714

[52] U.S. Cl. .................. 424/251; 260/256.4 F; 260/256.5 R
[51] Int. Cl.$^2$ ... C07D 471/04; 260 256.4 F;256.5 R
[58] Field of Search .................. 424/251

[56] References Cited

UNITED STATES PATENTS

| | | | |
|---|---|---|---|
| 3,414,574 | 12/1968 | Frey et al. | 260/256.4 F |
| 3,974,161 | 8/1976 | Althuis et al. | 260/256.4 F |

Primary Examiner—Donald G. Daus
Assistant Examiner—James H. Turnipseed
Attorney, Agent, or Firm—Connolly and Hutz

[57] ABSTRACT

A series of alkyl ester and amide derivatives of pyrimido[4,5-b]quinolin-4(3H)-one-2-carboxylic acids, salts thereof and their preparation and use as antiulcer agents.

27 Claims, No Drawings

ESTERS AND AMIDES OF PYRIMIDO[4,5-B]QUINOLIN-4(3H)-ONE-2-CARBOXYLIC ACIDS AS ANTIULCER AGENTS

BACKGROUND OF THE INVENTION

This invention relates to amide and alkyl ester derivatives of pyrimido[4,5-b]quinolin-4(3H)-one-2-carboxylic acids and salts thereof as agents for the control of peptic ulcers in animals, including man.

A number of pyrimido[4,5-b]quinolines (1,3-diazoacridines) are described in the art [*J. Chem. Soc.*, 727 (1927); *J. Hetero. Chem.*, 7, 99 (1970); *J. Am. Chem. Soc.*, 78, 5108 (1956); and *J. Chem. Soc.*, 552 (1948)]. However, none of them contain a carboxy group or functional derivative thereof, i.e., an ester, amide, acid chloride, with the exception of 2,4-dihydroxypyrimido[4,5-b]quinoline-5-carboxylic acid, its methyl ester, amide and acid chloride; 1,3-dimethyl-1,2,3,4-tetrahydro-pyrimido[4,5-b]quinoline-2,4-dione-5-carboxylic acid methyl ester; and 10-methyl-2,3,4,10-tetrahydro-pyrimido-[4,5-b]quinolin-2,4-dione-5-carboxylic acid and its methyl ester. The products were investigated as potential riboflavin antagonists. Taylor et al., *J. Am. Chem. Soc.*, 78, 5108 (1956) describe 2-methylpyrimido[4,5-b]-quinolin-4(3H)-one. No 2-carboxy substituted derivatives are described in the literature.

Belgian Patent No. 813,571, granted Oct. 11, 1974, describes pyrimido-[4,5-b]quinolin-4(3H)-one-2-carboxylic acids, esters and simple amides (—CONH$_2$) thereof, and corresponding 2-hydroxamic acids as antiallergy agents.

The compounds described herein are effective antiulcer agents via the intraperitoneal route of administration. Many of them are also active via the oral route of administration. These products not only accelerate healing of such ulcers but also prevent formation of ulcers and some decrease gastric acid output in animals, including humans. They can, therefore, be said to be useful for the control of gastric ulcers.

SUMMARY OF THE INVENTION

It has now been found that compounds having formula I are effective antiulcer agents in animals, including man. The compounds have the formula

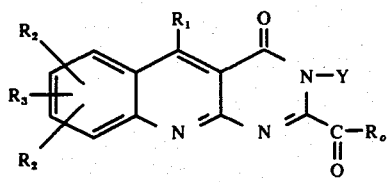

(I)

wherein
R$_0$ is selected from the group consisting of alkoxy having from one to four carbon atoms, and NHZ wherein Z is selected from the group consisting of hydrogen, hydroxyalkyl having from two to four carbon atoms, aminoalkyl having from two to four carbon atoms; alkyl having from one to four carbon atoms and:

—(alk)$_m$—(O)$_n$—W wherein (alk) is alkylene having from one to four carbon atoms, with the proviso that when $n$ is 1, (alk) is alkylene having from two to four carbon atoms;
W is selected from the group consisting of pyridyl, imidazolyl and

wherein
X is selected from the group consisting of hydrogen, amino, carboxy, hydroxy, alkyl having from one to four carbon atoms and alkoxy having from one to four carbon atoms;
each of $m$ and $n$ is 0 or 1, provided that when $n$ is 1, $m$ is 1;
Y is selected from the group consisting of hydrogen, methyl, carboxyalkyl having from one to four carbon atoms in the alkyl group and carbalkoxyalkyl having from one to four carbon atoms in each of the alkyl and alkoxy groups;
R$_1$ is selected from the group consisting of hydrogen, alkyl having from one to four carbon atoms and phenyl;
each of R$_2$, R$_3$ and R$_4$ when taken separately is selected from the group consisting of hydrogen, alkyl having from one to four carbon atoms, alkoxy having from one to four carbon atoms, halo, hydroxy, benzyloxy, benzoyloxy, alkanoyloxy having from one to four carbon atoms, thiol, methylthio, methylsulfinyl, benzylthio and benzylsulfinyl;
with the proviso that no more than two of R$_2$, R$_3$ and R$_4$ are branched alkyl or alkoxy, and when two of R$_2$, R$_3$ and R$_4$ are branched chain alkyl or alkoxy, said groups are located on non-adjacent positions;
R$_2$ and R$_3$ or R$_3$ and R$_4$ when taken together are alkylenedioxy and are selected from the group consisting of methylenedioxy and ethylenedioxy;
with the proviso that only one of said pairs is alkylenedioxy;
and the pharmaceutically-acceptable acid addition salts thereof, and the pharmaceutically-acceptable cationic salts of those compounds wherein W is carboxyphenyl or Y is carboxyalkyl.

By the term "pharmaceutically-acceptable acid addition salts" is meant salts with mineral acids such as hydrochloric and hydrobromic acids, organic acids such as acetic, propionic, butyric, benzoic, citric, maleic, fumaric, malic, glycolic, lactic, tartaric, 2-hydroxynaphthoic, sulfosalicylic and salicylic acids.

By the term "pharmaceutically-acceptable cationic salts" is meant salts such as the alkali metal salts, e.g., sodium and potassium, alkaline earth metal salts such as calcium and magnesium salts, aluminum salts, ammonium salts, and salts with organic bases, e.g., amine salts such as triethylamine, tri-n-butylamine, piperidine, N-ethylpiperidine, triethanolamine, diethylaminoethylamine, N,N'-dibenzylethylenediamine and pyrrolidine.

Compounds of the above formula wherein Z is hydroxyalkyl, aminoalkyl or —(alk)$_m$—(O)$_n$—W are new compounds.

The compounds of particular interest are those wherein up to two substituents are present in the benzenoid ring. Preferred compounds of this invention are those wherein:

a.
each of $R_1$, $R_2$, $R_3$, $R_4$ and Y is hydrogen;
$R_0$ is NHZ wherein Z is hydrogen or $-(alk)_m-(O)_n-W$;
each of m and n is 1; and
W is

wherein X is as defined above;

b.
each of $R_1$, $R_2$ and Y is hydrogen;
each of $R_3$ and $R_4$ is methoxy;
$R_0$ is $-NHZ$ wherein Z is hydrogen or $-(alk)_m-(O)_n-W$;
each of m and n is 1; and
W is

wherein X is as defined above;

c.
each of $R_1$ and $R_2$ is hydrogen;
each of $R_3$ and $R_4$ is methoxy;
Y is carbalkoxyalkyl;
$R_0$ is $-NHZ$ wherein Z is hydrogen or $-(alk)_m-(O)_n-W$;
m is 1;
n is 0 or 1; and
W is pyridyl.

Special interest exists in the following compounds under the above categories:
those under (a) wherein X is hydrogen or amino;
those under (b) wherein X is hydrogen or amino; and
those under (c) wherein n is 1.

DETAILED DESCRIPTION OF THE INVENTION

The compounds of this invention wherein $R_0$ is alkoxy are prepared according to methods described in Belgian Patent No. 813,571. The preferred method described therein for making the esters of formula I is illustrated by the sequence:

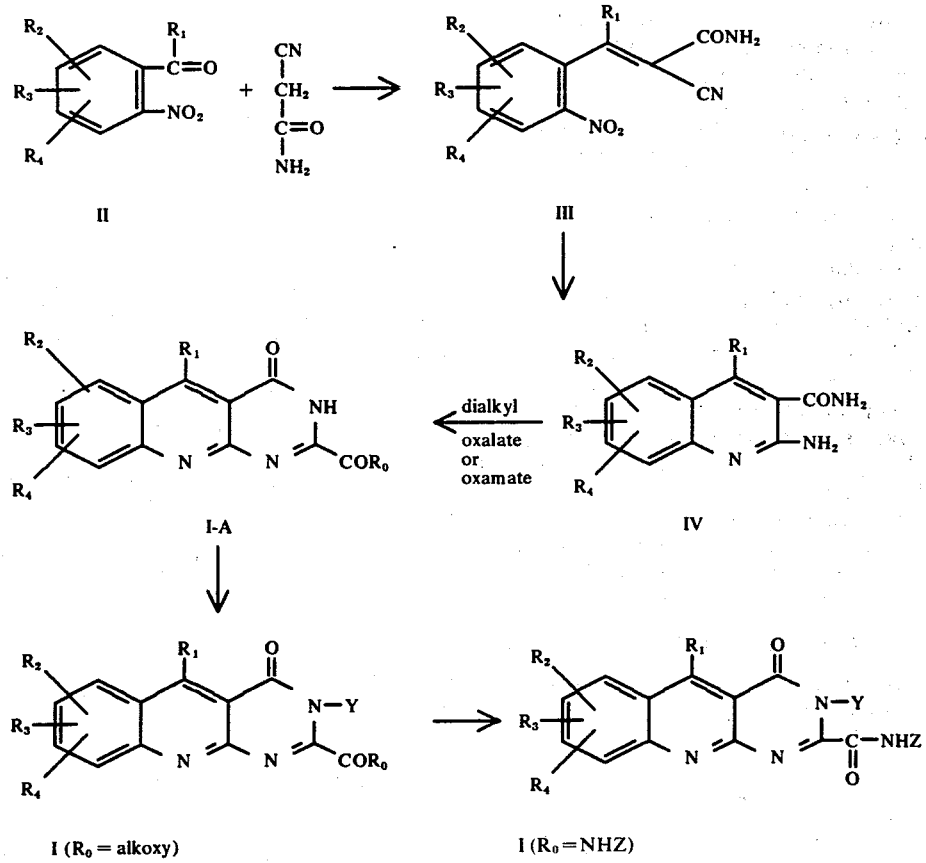

The appropriate 2-nitrobenzaldehyde derivative (formula II) is reacted with an active methylene nucleophile such as cyanoacetamide in a reaction-inert solvent, e.g., absolute ethanol, in the presence of a catalyst (sodium ethoxide, piperidine) at from about 0° to 50° C. The α-cyano-β-(2-nitrophenyl)acrylamide derivative (formula III) is then reduced by any of a variety of reagents such as metal-acid combinations (zinc-HCl, iron-acetic acid, zinc dust-alkali) or by catalytic hydrogenation. The reduced product cyclizes spontaneously to give the corresponding 2-aminoquinoline-3-carboxamide (formula IV) which is reacted with a dialkyl oxalate or alkyl oxamate to provide the tricyclic compound (formula I-A). Alkylation of the sodio derivative of formula I-A compounds with the appropriate Y-halide affords ester products of formula I ($R_0$ = alkoxy; Y ≠ H). Alternatively, intermediates of formula III can be alkylated in like manner to produce an N-(Y-substituted)-α-cyano-β-(2-nitrophenyl)acrylamide which, when carried through the sequence affords compounds of formula I wherein Y ≠ H.

Compounds of formula I wherein $R_0$ is NHZ are conveniently and preferably prepared from compounds of formula I wherein $R_0$ is alkoxy by amidation with the appropriate amine $H_2NZ$. The amidation can be conducted in a number of ways, such as by combining the reactants in a reaction-inert solvent such as chloroform, tetrahydrofuran, N,N-dimethylformamide or ethanol. The reaction is generally carried out at temperatures of from about 50° C. to the reflux temperature of the solvent. Temperatures of from about 50° to 100° C. are favored. The reaction is usually complete within a few hours depending primarily, of course, upon the nature of the reactants and the temperature. The product is recovered by removal of the solvent. The molar ratio of reactants should be at least 1:1 since when less than a molar equivalent of amine reactant per mole of ester reactant is used, incomplete amidation results. The favored molar ratio of ester to amine reactant is from about 1:2 to about 1:4. Larger excesses of amine appear to serve no advantage. This procedure, amidation in a reaction-inert solvent is favored, especially when the amine reactant is a solid at the reaction temperature or is not readily available.

A modification of the amidation comprises reacting the appropriate formula I ester and the appropriate amine in the "neat", that is, in the absence of a reaction-inert solvent. In this procedure an excess of the amine reactant is used to not only serve as solvent but also to assure maximum conversion of ester to amide. The reaction is carried out at a temperature of from about 50° to 150° C. and desirably at from about 75° to about 100° C. at atmospheric pressure. Of course, when the amine reactant is highly volatile (e.g., methylamine, ethylamine), the reaction is conducted in a sealed vessel such as a glass or stainless steel bomb. The product is recovered by suitable means as, for example, by dilution of the reaction mixture with a solvent in which the product is insoluble, e.g., chloroform, and filtration of the product. Alternatively, the excess amine is removed by evaporation under reduced pressure, by extraction or other suitable means, and the residue treated with hydrochloric acid to precipitate the hydrochloride salt of the product.

A further modification of the amidation reaction comprises reacting the appropriate ester with the appropriate amine or acid addition salt thereof, such as a hydrochloride salt, in a reaction-inert solvent in the presence of from a catalytic to an equivalent amount of a non-nucleophilic base (e.g., sodium hydride). Suitable solvents are chloroform, tetrahydrofuran and N,N-dimethylformamide. The molar ratio of ester to amine normally varies from about 1:1 to about 1:4. The product is recovered by conventional means such as filtration of insolubles, extraction with a suitable solvent and subsequent removal of the solvent.

Compounds of formula I wherein $R_0$ is —NHZ and Y is other than hydrogen are also prepared by the above-described methods from the appropriate Y-substituted esters of formula I. Alternatively, they are prepared by alkylation of the appropriate amide of formula I ($R_0$ = NHZ; Y = H) with the Y-halide, Y-tosylate or Y-mesylate. The sodio derivatives are readily obtained by reacting the appropriate formula I amide (Y = H) with a base such as sodium hydride in a suitable non-acidic solvent such as N,N-dimethylformamide or tetrahydrofuran.

Compounds of formula I wherein $R_2$, $R_3$ or $R_4$ are benzyloxy, benzylthio or methylthio serve as intermediates for compounds wherein $R_2$, $R_3$ or $R_4$ are hydroxy, alkanoyloxy, thiol, methylsulfinyl or benzylsulfinyl. Debenzylation is conveniently accomplished by treating the benzyl ether or benzylthio ether with trifluoroacetic acid or sulfuric acid. The debenzylated products are obtained as their trifluoroacetate salts. The hydroxy and thiol compounds, in turn, are intermediates for preparation of corresponding alkanoyloxy and benzyloxy derivatives by acylation using the appropriate acid anhydride, e.g., acetic anhydride. A catalytic amount of p-toluenesulfonic acid is generally used to expedite the reaction.

Compounds wherein any of $R_2$, $R_3$ or $R_4$ is benzylsulfinyl or methylsulfinyl are readily prepared from the corresponding thioether compounds by oxidation with an appropriate oxidizing agent such as hydrogen peroxide or a peracid such as m-chloroperbenzoic acid according to methods known to those skilled in the art. Combinations of methylsulfinyl or benzylsulfinyl with methylthio and/or benzylthio in the same compound are achieved by reacting, for example, a compound of formula III wherein at least two of $R_2$, $R_3$ or $R_4$ are chloro with sufficient sodium methyl (or benzyl) mercaptide to replace only one chloro substituent. A mixture of isomers is, of course, normally formed. The monomethyl (or benzyl) derivative is then oxidized to the sulfinyl derivative and the remaining chloro substituent or substituents replaced with methylthio or benzylthio in the manner described.

The required amine reactants ($H_2NZ$), if not already described in the literature, are readily obtainable by standard reactions. For example, when $H_2NZ$ is $H_2N$—(alk)—O—W wherein alk and W are as defined above, the required amines are prepared by the Williamson reaction of the appropriate alkanolamine and the appropriate Cl—W or Br—W reactant. Alternatively, they are prepared by conversion of the appropriate alkanoic acid amide compound (W—O—A—$CONH_2$) to the corresponding amine W—O—A—$CH_2NH_2$ by reaction with lithium aluminum hydride. (In the preceding two formulae, A represents the alkyl portion of the alkanoic acid amide.) The ether-amides W—O—A—$CONH_2$ are, in turn, prepared by the Williamson reaction of the appropriate chloro (or bromo) alkanoic acid amide and the appropriate phenol or alcohol, W—OH.

The compounds described herein are valuable antiulcer agents as previously noted. They are all active via the intraperitoneal route of administration and many of them are also active by the oral route of administration. They can be administered alone or in combination with a pharmaceutical carrier selected on the basis of the chosen route of administration and standard pharmaceutical practice. For example, they can be administered orally in the form of tablets containing such excipients as polyvinylpyrrolidone, a Carbowax (non-volatile, solid polyethylene glycols available from Carbide and Carbon Chemicals Corporation), especially Carbowax 6000, starch, milk sugar, etc., or in capsules alone or in admixture with the same or equivalent excipients. They may also be administered orally in the form of elixirs or oral suspensions which may contain flavoring or coloring agents or be injected parenterally; that is, for example, intramuscularly or subcutaneously. For parenteral administration, they are best used in the form of a sterile solution which may be either aqueous, such as water, isotonic dextrose, isotonic saline, Ringer's solution; or non-aqueous, such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compounds may include liquid diluents, for example, propylene glycol, diethyl carbonate, glycerol, sorbitol, etc.; buffering agents, as well as local anesthetics and inorganic salts to afford desirable pharmacological properties.

For both oral and intraperitoneal administration, a dosage range of from about 100 to about 700 mg. per day is effective. The dosage level can, with careful supervision, range up to as high as about three grams per day. Propylene glycol is a suitable and convenient carrier or diluent for intraperitoneal use. Carbowax 6000 is a favored excipient for oral use. Compositions containing from about 50 to about 90% by weight of polyvinylpyrrolidone or Carbowax 6000 are especially effective for oral administration. Higher or lower amounts of excipients can, of course, be used but appear to offer no advantages over these proportions. For intraperitoneal use, the polyvinylpyrrolidone formulations are suspended in carriers such as water, or in saline solution containing 1% carboxymethylcellulose and 0.1% Tween 80 (polyoxyethylene ethers of partial esters of fatty acids and hexitol anhydrides derived from sorbitol, available from Atlas Chemical Industries, Inc.). The water-soluble products of this invention are conveniently administered in water solution.

The effectiveness of the products of this invention as antiulcer agents is determined by the stressed rat assay as follows:

COLD-RESTRAINT STRESSED RAT

Non-fasted female rats (Charles River C-D strain) weighing 70–140 gms. are administered the drug or carrier (control animals) intraperitoneally or orally (in saline solution containing 1% carboxymethylcellulose and 0.1% (Tween 80) 3 hours before being lightly anesthetized with ether and taped in the supine position to individual sheets of plexiglass. After recovery from anesthesia, the restrained animals are positioned horizontally in a refrigerator maintained at 10°–12° C. and 3 hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination. Each stomach is then cut open along the greater curvature and the glandular portion (hind stomach) examined for damage. The number of gastric erosions, their severity and the color of the stomachs is recorded. The Mann-Whitney-Wilcoxon rank sum test is used to compare the median number of gastric erosions in the control group with the median number of gastric erosions in each drug-treated group to determine if they are statistically different (Dixon et al., "Introduction to Statistical Analysis," 3rd Ed., McGraw-Hill Book Company, New York, pp. 344–347, 1969).

The antiulcer activity of several compounds of this invention is presented below:

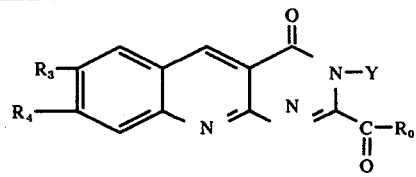

| $R_3$ | $R_4$ | Y | $R_0$ | Route[a] | Active at mg./kg. |
|---|---|---|---|---|---|
| H | H | H | $NH_2$ | i.p. | 32 |
| $CH_3O$ | $CH_3O$ | H | $NH_2$ | i.p. | 32 |
|  |  |  |  | p.o. | 32 |
|  |  |  |  | p.o. | 10 |
| $CH_3O$ | $CH_3O$ | H | $NHCH_3$ | i.p. | 32[b] |
| $CH_3O$ | $CH_3O$ | H | $NHC_2H_5$ | i.p. | 32[c] |
| $CH_3O$ | $CH_3O$ | H | $NHCH_2CH_2OH$ | i.p. | 32 |
|  |  |  |  | p.o. | 32 |
| H | H | H | $NHCH_2CH_2-O-(3-NH_2C_6H_4)$ | i.p. | 32 |
|  |  |  |  | p.o. | 32 |
| $CH_3O$ | $CH_3O$ | H | NH-(2-pyridyl) | i.p. | 32 |
| $CH_3O$ | $CH_3O$ | H | $NHCH_2CH_2$-(2-pyridyl) | i.p. | 32[b] |
| $CH_3O$ | $CH_3O$ | H | $NH(CH_2)_2-\overline{CH=CH-N=C}-NH$ | i.p. | 32[b] |
| $CH_3O$ | $CH_3O$ | H | $NHCH_2CH_2-O-C_6H_5$ | i.p. | 32 |
|  |  |  |  | i.p. | 10[b] |
| $CH_3O$ | $CH_3O$ | H | $NHCH_2CH_2-O-(3-NH_2C_6H_4)$ | i.p. | 32 |
|  |  |  |  | p.o. | 32 |
|  |  |  |  | p.o. | 10 |
| $CH_3O$ | $CH_3O$ | H | $NHCH_2CH_2-O-(2-pyridyl)$ | i.p. | 32[b] |
| $CH_3O$ | $CH_3O$ | $CH_2COOH$ | $NHCH_2CH_2-O-C_6H_5$ | i.p. | 32[b] |
| $CH_3O$ | $CH_3O$ | $CH_2COOC_2H_5$ | $NHCH_2CH_2-O-(2-pyridyl)$ | i.p. | 32 |
|  |  |  |  | p.o. | 32 |
| $CH_3O$ | $CH_3O$ | $CH_3$ | $NH_2$ | i.p. | 32 |
|  |  |  |  | p.o. | 32 |
| $CH_3O$ | $CH_3O$ | $(CH_2)_3COOC_2H_5$ | $OC_2H_5$ | i.p. | 32[b] |
| $CH_3O$ | $CH_3O$ | $CH_2COOC_2H_5$ | $OC_2H_5$ | i.p. | 32[b] |
| H | H | H | $OC_2H_5$ | p.o. | 100[b] |

-continued

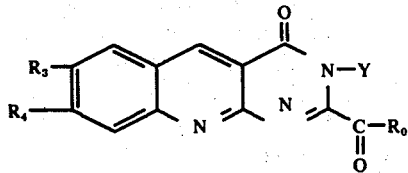

| R₃ | R₄ | Y | R₀ | Route[a] | Active at mg./kg. |
|---|---|---|---|---|---|
| CH₃O | CH₃O | H | OC₂H₅ | p.o. | {32, 10[d]} |

[a]i.p. = intraperitoneal; p.o. = oral
[b]inactive orally at 32 mg./kg.
[c]inactive orally at 25 mg./kg.
[d]inactive intraperitoneally at 10 mg./kg.

EXAMPLE 1

7,8-Dimethoxypyrimido[4,5-b]quinolin-4(3H)-one-2-carboxamide

Anhydrous ammonia is bubbled into a mixture of ethyl 7,8-dimethoxy-pyrimido[4,5-b]quinolin-4(3H)-one-2-carboxylate (300 mg., 9.00 millimoles) in absolute ethanol (75 ml.) for 15 minutes. A clear solution formed, followed, after a few minutes, by formation of a precipitate. The reaction mixture is transferred to a pressure bomb (Monel) and heated in a 95° C. oil bath overnight. The bomb is then cooled to room temperature and the contents removed. The bomb is washed with ethanol and the combined reaction mixture plus wash filtered to recover the product. The filter cake is washed with ethanol and then dried in air. Yield = 260 mg. (95%); m.p. 310° C. (dec.)

EXAMPLE 2

N-(2-Phenoxyethyl)-7,8-Dimethoxypyrimido[4,5-b]quinolin-4(3H)-one-2-carboxamide A mixture of ethyl 7,8-dimethoxypyrimido[4,5-b]quinolin-4(3H)-one-2-carboxylate (0.987 g., 3.00 mM) and 2-phenoxyethylamine (1.23 g., 9.00 mM) is heated and stirred at 90° C. for 3 hours. The mixture is then cooled to room temperature and diluted with chloroform (50 ml.) to precipitate the product. It is dried in vacuo; yield = 0.82 g. (55%); m.p. 267°–269° C.

Analysis: Calc'd for $C_{22}H_{20}N_4O_5$: C, 62.87; H, 4.79; N, 13.32 %. Found: C, 62.47; H, 4.72; N, 13.10 %.

NMR $\delta_{CF_3CO_2D}^{TMS}$ : 3.58–4.66 (M,11,CH₂CH₂ and 2-OCH₃ at 4.23 and 4.31); 6.83–7.58 (M,5,phenyl); 7.76 (BS,2,H₆ and H₉-aromatic); 9.70 (S,1,H₅-aromatic).

By means of the above procedure, but replacing 2-phenoxyethylamine with the appropriate amine, the following compounds are prepared:

N-(2-Pyridylethyl)-7,8-dimethoxypyrimido[4,5-b]quinolin-4(3H)-one-2-carboxamide.

It is purified by recrystallization from chloroform; m.p. 264°–267° C.

MS (molecular ion) = 405.

Analysis: Calc'd for $C_{21}H_{19}N_5O_4$: C, 60.86; H, 4.86; N, 16.90 %. Found: C, 60.86; H, 4.52; N, 17.08 %.

NMR $\delta_{CF_3CO_2D}^{TMS}$ : 3.50–4.00 (BD,2,CH₂); 4.00–4.55 (M,8,CH₂ and 2-OCH₃); 8.00–8.93 (M,4,pyridine aromatic); 9.76 (S,1,H₅-aromatic).

N-(2-Pyridyl)-7,8-dimethoxypyrimido[4,5-b]quinolin-4(3H)-one-2-carboxamide.

The product is recrystallized from chloroform; m.p. >300° C.

MS (molecular ion) = 377.

NMR $\delta_{CF_3CO_2D}^{TMS}$ : 4.25 (S,3,OCH₃); 4.37 (S,3,OCH₃); 7.27–8.60 (M,6, H₆ and H₉ and pyridine aromatics); 9.73 (S,1,H₅-aromatic).

N-(3-Amino-2-phenoxyethyl)-7,8-dimethoxypyrimido[4,5-b]quinolin-4(3H)-one-2-carboxamide.

Recrystallization from chloroform affords the pure product; m.p. 233°–236° C.

MS (molecular ion) = 435.

Analysis: Calc'd for $C_{22}H_{21}N_5O_5 \cdot 1.5\ H_2O$: C, 57.13; H, 5.23; N,15.14%. Found: C, 57.59; H, 4.86; N, 15.00%.

NMR $\delta_{CF_3CO_2D}^{TMS}$ : 3.66–4.66 (M,10,CH₂CH₂ and 2-OCH₃ at 4.25 and 4.33); 7.00–7.91 (M,6,H₆ and H₉ and 4-phenyl aromatics); 8.86 (BS,2,—NH₂); 9.73 (S,1,H₅-aromatic).

EXAMPLE 3

N-Methyl-7,8-dimethoxypyrimido[4,5-b]quinolin-4(3H)-one-2-carboxamide

A mixture of ethyl 7,8-dimethoxypyrimido[4,5-b]quinolin-4(3H)-one-2-carboxylate (300 mg., 0.90 mM) and ethanol (75 ml.) saturated with anhydrous monomethylamine is heated at 95° C. for 24 hours in a stainless steel bomb. The bomb and contents are cooled, the contents removed and concentrated to dryness under reduced pressure. The residue is recrystallized from chloroform/ethyl acetate to give 250 mg. (88%) of product, m.p. 334° C. (dec.).

MS (molecular ion): 314

NMR $\delta_{CF_3CO_2D}^{TMS}$ : 3.26 (S,3,N-CH₃); 4.26 (S,3,OCH₃); 4.35 (S,3OCH₃); 7.80 and 7.83 (2-S,2,H₆ and H₉-aromatic); 9.8 (S,1,H₅-aromatic).

EXAMPLE 4

N-Ethyl-7,8-dimethoxypyrimido[4,5-b]quinolin-4(3H)-one-2-carboxamide Hydrochloride Dihydrate A stainless steel bomb is charged with a mixture of anhydrous ethylamine (50 ml.) and ethyl 7,8-dimethoxypyrimido[4,5-b]quinolin-4(3H)-one-2-carboxylate (1.00 g., 3.00 mM) and heated at 85° C. for 18 hours. It is then cooled to room temperature, the contents removed and acidified with 10% hydrochloric acid to pH 2. The hydrochloride salt precipitates and is isolated by filtration. Recrystallization from methanol gives 0.181 g. (18%) of product; m.p. 237°–238° C. (dec.).

MS (molecular ion): 328.

Analysis: Calc'd for $C_{16}H_{16}N_4O_4 \cdot HCl \cdot 2H_2O$: C, 47.95; H, 5.28; N, 13.98; Cl, 8.84 %. Found: C, 48.41; H, 4.79; N, 13.52; Cl, 8.10 %.

NMR $\delta_{CF_3CO_2D}^{TMS}$: 1.46 (T,3,J = 7 Hz,CH$_3$); 3.78 (Q,2,J = 7 Hz,CH$_2$); 4.25 (S,3,OCH$_3$); 4.36 (S,3,OCH$_3$); 7.80 and 8.03 (2-S,2,H$_6$ and H$_9$ aromatic); 9.8 (S,1,H$_5$-aromatic).

EXAMPLE 5

N-[2-(2-Pyridyloxy)ethyl]3-Carbethoxymethyl-7,8-dimethoxypyrimido[4,5-b]quinolin-4(3H)-one-2-carboxamide A solution of ethyl 3-carbethoxymethyl-7,8-dimethoxypyrimido[4,5-b]quinolin-4(3H)-one-2-carboxylate (0.415 g., 1mM) and 2-(2-pyridyloxy)ethylamine (0.276 g., 2 mM) in chloroform (10 ml.) is refluxed for 24 hours. It is then cooled to room temperature and concentrated in vacuo. The residue, an oil, is crystallized by addition of ether until precipitation is complete. Yield = 0.41 g. (81%) of product; m.p. 170°–180° C.

MS (molecular ion): 507.

Analysis: Calc'd for $C_{25}H_{25}N_5O_7$: C, 59.16; H, 4.96; N, 13.80 % Found: C, 58.58; H, 5.03; N, 14.19 %

NMR $\delta_{CF_3CO_2D}^{TMS}$: 1.53 (T,3,J = 7, CH$_3$); 4.16–5.16 (M,12,3-CH$_2$ and 2-OCH$_3$ at 4.35 and 4.45); 5.66 (BS,2, —CH$_2$CO$_2$—); 7.56–8.00 (M,4,H$_6$,H$_9$ and 2 pyridine aromatics); 8.33–8.93(M,2,2-pyridine aromatics); 9.80 (S,1,H$_5$-aromatic).

EXAMPLE 6

N-[2-(3-Aminophenoxy)ethyl] Pyrimido[4,5-b]quinolin-4(3H)-one-2-carboxamide

Repetition of the procedure of Example 5 but using the appropriate amine in place of 2-(2-pyridyloxy)ethylamine affords the following compounds:

N-[2-(2-aminophenoxy)ethyl] pyrimido[4,5-b]quinolin-4(3H)-one-2-carboxamide.

It is purified by recrystallization from chloroform; m.p. 250°–252° C.

MS (molecular ion): 375.

Analysis: Calc'd for $C_{20}H_{17}N_5O_3$: C, 63.99; H, 4.57; N, 18.66 %. Found: C, 63.22; H, 4.48; N, 18.81 %.

NMR $\delta_{CF_3CO_2D}^{TMS}$: 4.00–4.58 (M,4,CH$_2$); 7.00–9.00 (M,8,aromatics); 10.11 (S,1,H$_5$-aromatic).

N-(2-hydroxyethyl) 7,8-dimethoxypyrimido[4,5-b]quinolin-4(3H)-one-2-carboxamide.H$_2$NCH$_2$CH$_2$OH.H$_2$O.

It is purified by recrystallization from chloroform; m.p. 311°–313° C.

NMR $\delta_{CF_3CO_2D}^{TMS}$: 3.36–4.43 (M,14,methylenes and 2-OCH$_3$ at 4.25 and 4.36); 7.80 (S,2,H$_6$ and H$_9$-aromatics); 9.76 (S,1,H$_5$-aromatic).

Analysis: Calc'd for $C_{16}H_{16}N_4O_5 \cdot H_2NCH_2CH_2OH \cdot H_2O$: C, 51.05; H, 5.95; N, 16.54 %. Found: C, 51.64; H, 5.15; N, 15.64 %.

The ethanolamine is removed by treatment of the product with an equimolar amount of dilute hydrochloric acid. N-[2-(2-pyridyloxy)ethyl]pyrimido[4,5-b]quinolin-4(3H)-one-2-carboxamide.

It is recrystallized from chloroform; m.p. 270°–273° C.

NMR $\delta_{CF_3CO_2D}^{TMS}$: 4.26–5.16 (M,10,2-CH$_2$ and 2-OCH$_3$ at 4.33 and 4.43); 7.56–8.00 (M,4,H$_6$,H$_9$ and 2-pyridine aromatics); 8.41–9.00 (M,2,pyridine aromatic); 9.85 (S,1,H$_5$-aromatic).

EXAMPLE 7

N-[2-(4 or 5 -imidazolyl)ethyl] 7,8-Dimethoxypyrimido[4,5-b]quinolin-4(3H)-one-2-carboxamide A mixture of histamine dihydrochloride (2.0 g., 11 mM), ethyl 7,8-dimethoxypyrimido[4,5-b]quinolin-4(3H)-one-2-carboxylate (1.64 g., 5 mM) and N,N-dimethylformamide (10 ml.) is refluxed under dry nitrogen for 3 hours. The reaction mixture is cooled to room temperature and the resulting precipitate separated by filtration. The filter cake is washed first with chloroform and then with water. It is dried at 80° C. Yield = 0.964 g. (47%); m.p. 268°–271° C.

Analysis: Calc'd for $C_{19}H_{18}N_6O_4$: C, 55.33; H, 4.88; N, 20.37 %. Found: C, 55.46; H, 4.62; N, 19.58 %.

NMR $\delta_{CF_3CO_2D}^{TMS}$: 3.16–3.66 (M,2,methylene); 3.83–4.50 (M,CH$_2$ and 2-OCH$_3$ at 4.28 and 4.38); 7.50 (S,1,5-imidazole aromatic); 7.81 (S,2,H$_6$ and H$_9$-aromatic); 8.70 (S,1,2-imidazole aromatic); 9.76 (S,1,H$_5$-aromatic).

EXAMPLE 8

N-(2-Phenoxyethyl) 3-(Carboxymethyl)-7,8-Dimethoxypyrimido[4,5-b]quinolin-4(3H)-one-2-carboxamide A mixture of sodium hydride (0.22 g., 4.6 mM of 50%); N-(2-phenoxyethyl) 7,8-dimethoxypyrimido[4,5-b]quinolin-4(3H)-one-2-carboxamide (1.0 g., 2.2 mM); bromoacetic acid (0.319 g., 2.3 mM) and N,N-dimethylformamide (50 ml.) is refluxed for 6 hours and then cooled to room temperature. The precipitate which forms is separated by filtration and dried under vacuum to give 0.476 g. (43%) of product; m.p. 310°–315° C.

Analysis: Calc'd for $C_{24}H_{22}N_4O_7 \cdot \frac{1}{2} H_2O$: C, 59.13; H, 4.75; N, 11.49%. Found: C, 58.64; H, 4.26; N, 12.09%.

NMR $\delta_{CF_3CO_2D}^{TMS}$: 3.83–4.58 (M,12,2-CH$_2$, 2-OCH$_3$ at 4.23 and 4.31 and —NCH$_2$CO$_2$-methylene at 4.53); 6.83–7.55 (M,5,phenyl aromatics); 7.75 (BS,2,H$_6$ and H$_9$-aromatic); 9.70 (S,1,H$_5$-aromatic).

EXAMPLE 9

The following compounds are prepared from appropriate alkyl pyrimido[4,5-b]quinolin-4(3H)-one-2-carboxylates and appropriate amines, H$_2$NZ, by the procedures of Examples 1 (for volatile amines, e.g., NH$_3$, CH$_3$NH$_2$) or 2:

| | | | | | |
|---|---|---|---|---|---|
| R₁ | R₂' | R₃' | R₄' | R₅' | Z |
| C₆H₅ | H | H | H | H | CH₃ |
| H | H | H | H | H | n-C₄H₉ |
| H | H | H | H | H | t-C₄H₉ |
| H | H | OCH₃ | OCH₃ | H | n-C₄H₉ |
| H | H | OCH₃ | H | OCH₃ | CH₃ |
| H | H | H | OCH₃ | H | i-C₃H₇ |
| H | OCH₃ | H | H | OCH₃ | CH₃ |
| H | OCH₃ | H | H | OCH₃ | n-C₃H₇ |
| H | H | OCH₃ | OCH₃ | OCH₃ | C₂H₅ |
| H | H | OC₂H₅ | O-n-C₄H₉ | H | C₂H₅ |
| H | H | OC₂H₅ | OC₇H₇ | H | CH₃ |
| H | H | OC₂H₅ | OC₇H₇ | H | n-C₄H₉ |
| H | H | OC₂H₅ | OC₂H₅ | H | CH₃ |
| H | H | OC₂H₅ | OC₂H₅ | H | i-C₄H₉ |
| C₆H₅ | H | OC₇H₇ | OCH₃ | H | CH₃ |
| H | H | OCH₃ | OC₇H₇ | H | CH₃ |
| n-C₄H₉ | H | OC₇H₇ | H | H | C₂H₅ |
| CH₃ | H | —OCH₂CH₂O— | | H | n-C₄H₉ |
| H | H | —OCH₂CH₂O— | | H | C₂H₅ |
| C₆H₅ | H | F | OC₇H₇ | H | CH₃ |
| H | H | H | F | H | C₂H₅ |
| H | H | H | F | H | n-C₄H₉ |
| H | H | Cl | H | H | C₂H₅ |
| C₂H₅ | Cl | H | H | H | CH₃ |
| H | H | OCH₃ | H | H | t-C₄H₉ |
| CH₃ | H | H | OCH₃ | OCH₃ | CH₃ |
| C₆H₅ | H | H | OCH₃ | OCH₃ | i-C₃H₇ |
| C₆H₅ | H | OH | OCH₃ | H | C₂H₅ |
| n-C₄H₉ | H | OH | H | H | CH₃ |
| H | H | OCH₃ | OH | H | CH₃ |
| CH₃ | H | OCH₃ | OH | H | n-C₄H₉ |
| n-C₄H₉ | H | OH | H | H | C₂H₅ |
| H | H | H | H | H | CH₂CH₂OH |
| C₆H₅ | H | OCH₃ | OCH₃ | H | (CH₂)₄OH |
| H | H | H | H | H | (CH₂)₂OH |
| n-C₄H₉ | H | H | H | H | (CH₂)₂CH(OH)CH₃ |
| CH₃ | H | OCH₃ | OCH₃ | H | (CH₂)₄OH |
| H | H | OC₂H₅ | OC₂H₅ | H | CH₂CH₂OH |
| H | H | OCH₃ | OC₇H₇ | H | CH₂CH₂OH |
| CH₃ | H | OCH₃ | OC₇H₇ | H | CH₂CH(CH₃)CH₂OH |
| H | H | OC₇H₇ | OCH₃ | H | (CH₂)₃OH |
| CH₃ | H | —OCH₂CH₂O— | | H | CH₂CH₂OH |
| H | H | —OCH₂CH₂O— | | H | (CH₂)₄OH |
| C₆H₅ | H | F | OC₇H₇ | H | CH₂CH₂OH |
| H | H | H | F | H | (CH₂)₅OH |
| H | H | Cl | H | H | (CH₂)₃OH |
| C₆H₅ | H | —O—CH₂—O— | | H | CH₃ |
| H | OCH₃ | H | H | OCH₃ | CH₂CH₂OH |
| H | H | OCH₃ | OCH₃ | OCH₃ | CH₂CH₂OH |
| n-C₃H₇ | H | Cl | H | H | CH₂CH(CH₃)CH₂OH |
| H | OCH₃ | —OCH₂O— | | H | CH₂CH₂OH |
| H | OCH₃ | —OCH₂O— | | H | (CH₂)₄OH |
| C₂H₅ | —OCH₂O— | | H | H | (CH₂)₃OH |
| C₆H₅ | —OCH₂O— | | OCH₃ | H | CH₂CH₂OH |
| H | Br | H | H | H | CH₂CH(C₂H₅)OH |
| H | Cl | H | H | Cl | CH₂CH₂OH |
| H | CH₃ | H | H | H | (CH₂)₄OH |
| H | H | n-C₃H₇ | n-C₃H₇ | H | (CH₂)₃OH |
| H | H | t-C₄H₉ | H | H | CH₂CH(CH₃)OH |
| H | H | H | H | H | CH₂CH₂NH₂ |
| C₆H₅ | H | H | H | H | (CH₂)₄NH₂ |
| H | H | OCH₃ | OCH₃ | H | CH₂CH₂NH₂ |
| CH₃ | H | OCH₃ | OCH₃ | H | (CH₂)₃NH₂ |
| H | H | OCH₃ | OCH₃ | OCH₃ | (CH₂)₃NH₂ |
| H | H | OC₇H₇ | H | H | CH₂CH₂NH₂ |
| C₆H₅ | H | OC₇H₇ | OCH₃ | H | CH₂CH₂NH₂ |
| CH₃ | H | OC₇H₇ | OCH₃ | H | CH₂CH₂NH₂ |
| H | H | OCH₃ | OCH₂H₇ | H | (CH₂)₃NH₂ |
| CH₃ | H | —OCH₂CH₂O— | | H | CH₂CH₂NH₂ |
| H | H | —OCH₂CH₂O— | | H | (CH₂)₄NH₂ |
| H | —OCH₂O— | | OCH₃ | H | (CH₂)₃NH₂ |
| H | —OCH₂O— | | OCH₃ | H | (CH₂)₃NH₂ |
| H | H | Cl | H | Cl | CH₂CH₂NH₂ |
| CH₃ | H | Cl | Br | Cl | (CH₂)₄NH₂ |
| H | H | F | H | H | CH₂CH₂NH₂ |
| H | CH₃ | H | H | H | (CH₂)₃NH₂ |
| H | H | n-C₃H₇ | H | H | CH₂CH₂NH₂ |
| H | H | t-C₄H₉ | H | H | (CH₂)₄NH₂ |
| H | OC₇H₇ | H | H | H | CH₂CH₂NH₂ |
| H | H | OC₇H₇ | OCH₃ | H | CH₂CH₂NH₂ |
| C₆H₅ | H | OH | OCH₃ | H | CH₂CH₂NH₂ |

-continued

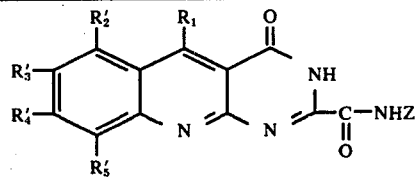

| R₁ | R₂' | R₃' | R₄' | R₅' | Z |
|---|---|---|---|---|---|
| CH₃ | H | OCH₃ | OH | H | (CH₂)₃NH₂ |
| H | H | OH | H | H | CH₂CH₂NH₂ |
| H | H | OH | H | H | (CH₂)₃NH₂ |
| H | H | OH | OCH₃ | H | CH₂CH₂OH |
| H | H | SCH₃ | H | H | CH₃ |
| n-C₄H₉ | H | SCH₃ | H | H | n-C₃H₇ |
| H | H | SCH₃ | H | H | CH₂CH₂OH |
| C₆H₅ | H | SCH₃ | H | H | (CH₂)₄OH |
| H | H | SCH₃ | H | H | CH₂CH₂NH₂ |
| H | H | SCH₃ | SCH₃ | H | C₂H₅ |
| C₂H₅ | H | SCH₃ | SCH₃ | H | CH₂CH(CH₃)CH₂OH |
| C₂H₅ | H | SCH₃ | SCH₃ | H | (CH₂)₄NH₂ |
| H | H | SC₇H₇ | H | H | C₂H₅ |
| H | H | SC₇H₇ | C₂H₅ | H | n-C₄H₉ |
| H | H | H | SC₇H₇ | H | CH₃ |
| CH₃ | H | H | SC₇H₇ | H | n-C₄H₉ |
| H | SC₇H₇ | H | H | SC₇H₇ | C₂H₅ |
| C₆H₅ | H | SC₇H₇ | H | H | CH₂CH₂OH |
| i-C₃H₇ | H | H | SC₇H₇ | H | (CH₂)₄OH |
| H | SC₇H₇ | H | H | SC₇H₇ | (CH₂)₃OH |
| C₆H₅ | H | SC₇H₇ | C₂H₅ | H | CH₂CH₂NH₂ |
| H | H | H | SC₇H₇ | H | (CH₂)₄NH₂ |
| H | H | SOCH₃ | H | H | CH₃ |
| H | H | SOCH₃ | SOCH₃ | H | i-C₃H₇ |
| n-C₄H₉ | H | SOCH₃ | H | H | n-C₃H₇ |
| H | H | SOC₇H₇ | H | H | C₂H₅ |
| CH₃ | H | H | SOC₇H₇ | H | t-C₄H₉ |
| H | H | SOCH₃ | H | H | CH₂CH₂OH |
| C₆H₅ | H | SOCH₃ | SOCH₃ | H | (CH₂)₄OH |
| i-C₃H₇ | H | H | SOC₇H₇ | H | CH₂CH₂NH₂ |
| H | H | SOC₇H₇ | C₂H₅ | H | (CH₂)₄NH₂ |
| C₆H₅ | H | SOC₇H₇ | H | H | (CH₂)₃NH₂ |
| H | H | SH | H | H | C₂H₅ |
| CH₃ | H | SH | H | H | C₂H₅ |
| H | H | SH | C₂H₅ | H | n-C₄H₉ |
| H | SH | H | H | SH | C₂H₅ |
| H | H | H | SH | H | CH₃ |
| CH₃ | H | H | SH | H | n-C₄H₉ |
| H | H | SH | H | H | CH₂CH₂OH |
| H | H | SH | H | H | (CH₂)₄OH |
| C₂H₅ | H | SH | H | H | CH₂CH₂NH₂ |
| H | H | H | SH | H | (CH₂)₄NH₂ |
| CH₃ | H | H | H | H | CH₃ |
| CH₃ | H | H | H | H | i-C₃H₇ |
| CH₃ | H | H | H | H | n-C₄H₉ |
| n-C₄H₉ | H | H | H | H | C₂H₅ |
| CH₃ | H | OCH₃ | OCH₃ | H | C₂H₅ |
| CH₃ | H | H | H | H | n-C₃H₇ |
| n-C₃H₇ | H | Cl | H | H | CH₃ |
| CH₃ | CH₃ | CH₃ | CH₃ | OCH₃ | i-C₃H₇ |
| CH₃ | H | H | OC₂H₅ | OC₂H₅ | CH₃ |
| C₆H₅ | H | H | H | H | C₂H₅ |
| C₆H₅ | H | H | OCH₃ | H | i-C₄H₉ |
| C₆H₅ | H | Cl | Cl | H | n-C₄H₉ |
| CH₃ | H | H | H | H | (CH₂)₃OH |
| C₂H₅ | H | OCH₃ | OCH₃ | H | (CH₂)₃OH |
| C₆H₅ | H | CH₃ | Cl | H | CH₂CH₂OH |
| C₆H₅ | H | H | H | H | CH₂CH₂NH₂ |
| C₆H₅ | H | H | CH₃ | H | (CH₂)₄NH₂ |
| H | H | Cl | Cl | H | C₂H₅ |
| H | H | SCH₃ | Cl | H | C₂H₅ |
| H | H | SOCH₃ | Cl | H | C₂H₅ |
| H | H | SOCH₃ | SC₇H₇ | H | C₂H₅ |
| H | H | Cl | SCH₃ | H | C₂H₅ |
| H | H | Cl | SOCH₃ | H | C₂H₅ |
| H | H | SCH₃ | SOCH₃ | H | C₂H₅ |
| H | H | SC₇H₇ | Cl | H | C₂H₅ |
| H | H | SC₇H₇ | SCH₃ | H | C₂H₅ |
| H | H | SH | SCH₃ | H | C₂H₅ |

EXAMPLE 10

Ethyl 7-Acetoxy-8-Methoxypyrimido[4,5-b]Quinolin-4(3H)-One-2-(N-Ethylcarboxamide)p-Toluenesulfonate A mixture of acetic anhydride (4 ml.), 7-hydroxy-8-methoxypyrimido[4,5-b]quinolin-4(3H)one-2-(N-ethylcarboxamide) (157 mg. 0.5 mmole) and p-toluenesulfonic acid monohydrate (95 mg., 0.5 mmole) is heated at 100° C. for 24 hours. The acetic anhydride is then stripped from the reaction mixture in vacuo. The solid residue is dissolved in hot chloroform and the solution decolorized with activated charcoal. Benzene (4 volumes) is added to the decolorized solution which is then chilled in ice. The crystals which separate are recovered by filtration and air dried.

The above procedure is repeated but using the appropriate acid anhydride in place of acetic anhydride and the appropriate hydroxy compound as reactant to give the following compounds:

| $R_1$ | $R_2'$ | $R_3'$ | $R_4'$ | $R_5'$ | Z |
|---|---|---|---|---|---|
| H | H | $OCH_3$ | $OCOC_3H_7$ | H | $CH_3$ |
| H | H | $OCOCH_3$ | $OCH_3$ | H | $CH_3$ |
| $C_6H_5$ | H | $OCOCH_3$ | $OCH_3$ | H | $C_2H_5$ |
| H | H | OCOH | H | H | $C_2H_5$ |
| H | H | $OCH_3$ | $OCOCH_3$ | H | $CH_3$ |
| H | $OCOC_3H_7$ | $OCH_3$ | H | H | $C_2H_5$ |
| H | H | $OCOC_6H_5$ | H | H | $CH_3$ |
| H | H | H | $OCOC_6H_5$ | H | $n-C_4H_9$ |
| H | H | $OCOC_6H_5$ | $OCH_3$ | H | $CH_2CH_2OH$ |
| H | H | Cl | $OCOC_6H_5$ | H | $CH_2CH(CH_3)CH_2OH$ |
| H | H | $OCH_3$ | $OCOC_6H_5$ | H | $(CH_2)_3NH_2$ |
| H | H | F | $OCOC_6H_5$ | H | $(CH_2)_6NH_2$ |
| $C_6H_5$ | H | $OCOCH_3$ | H | H | $C_2H_5$ |
| $n-C_4H_9$ | H | $OCOC_6H_5$ | $OCH_3$ | H | $CH_3$ |
| $C_6H_5$ | H | F | $OCOCH_3$ | H | $CH_3$ |
| $CH_3$ | H | $OCOC_6H_5$ | $OCH_3$ | H | $(CH_2)_3NH_2$ |
| $n-C_4H_9$ | $C_2H_5$ | $OCOCH_3$ | H | H | $(CH_2)_4NH_2$ |
| $C_6H_5$ | H | $OCOCH_3$ | $OCH_3$ | H | $CH_2CH_2NH_2$ |
| $C_6H_5$ | H | $OCOC_6H_5$ | $OCH_3$ | H | $CH_2CH_2NH_2$ |
| $CH_3$ | H | $OCH_3$ | $OCOC_6H_5$ | H | $(CH_2)_3NH_2$ |
| H | H | $OCOC_2H_5$ | H | H | $CH_2CH_2NH_2$ |
| H | H | $OCOCH_3$ | $OCH_3$ | H | $CH_2CH_2OH$ |
| H | H | $OCOCH_3$ | H | H | $C_2H_5$ |

EXAMPLE 11

The following compounds are prepared from appropriate alkyl pyrimido[4,5-b]quinolin-4(3H)-one-2-carboxylates and appropriate amines $H_2NZ$ according to the procedure of Example 5.

| $R_1$ | $R_2'$ | $R_3'$ | $R_4'$ | $R_5'$ | Z |
|---|---|---|---|---|---|
| H | H | H | H | H | $CH_2CH_2-O-(4-H_2NC_6H_4)$ |
| $C_6H_5$ | H | H | H | H | $CH_2CH_2-O-C_6H_5$ |
| $CH_3$ | H | H | H | H | $(CH_2)_3-O-C_6H_5$ |
| H | H | H | H | H | $(CH_2)_4-O-C_6H_5$ |
| H | H | $OCH_3$ | $OCH_3$ | H | $CH_2CH_2-O-(4-CH_3C_6H_4)$ |
| H | H | H | H | H | $(CH_2)_3-O-(4-n-C_4H_9C_6H_4)$ |
| $C_6H_5$ | H | H | H | H | $CH_2CH_2-O-(2-CH_3OC_6H_4)$ |
| H | H | H | $OCH_3$ | H | $(CH_2)_3-O-(3-C_2H_5C_6H_4)$ |
| H | H | H | H | H | $CH_2CH_2-O-(4-n-C_4H_9OC_6H_4)$ |
| $4-C_4H_9$ | H | H | H | H | $CH_2CH_2-O-(2-HOC_6H_4)$ |
| H | H | H | H | H | $(CH_2)_3-O-(4-HOC_6H_4)$ |
| H | H | H | H | H | $CH_2CH_2-O-(4-HOOCC_6H_4)$ |
| $C_6H_5$ | H | $OCH_3$ | $OCH_3$ | H | $(CH_2)_4-O-(3-HOOCC_6H_4)$ |
| $C_6H_5$ | H | $OC_7H_7$ | $OCH_3$ | H | $CH_2CH_2-O-(3-H_2NC_6H_4)$ |
| H | H | $OCH_3$ | OH | H | $CH_2CH_2-O-(3-H_2NC_6H_4)$ |
| H | H | $-OCH_2CH_2O-$ | | H | $CH_2CH-O-C_6H_5$ |
| $CH_3$ | H | $-OCH_2CH_2O-$ | | H | $(CH_2)_3-O-(4-HOC_6H_4)$ |
| H | $-OCH_2O-$ | | $OCH_3$ | H | $CH_2CH_2-O-(2-H_2NC_6H_4)$ |
| $C_6H_5$ | $-OCH_2O-$ | | $OCH_3$ | H | $(CH_2)_3-O-(4-HOOCC_6H_4)$ |
| H | $-OCH_2O-$ | | $OCH_3$ | H | $(CH_2)_4-O-(3-CH_3C_6H_4)$ |
| $n-C_4H_9$ | $OC_7H_7$ | $OCH_3$ | $OCH_3$ | H | $CH_2CH_2-O-C_6H_5$ |

-continued

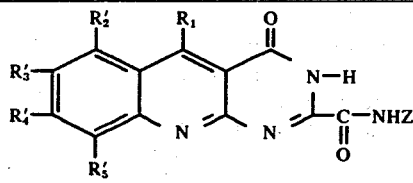

| $R_1$ | $R_2'$ | $R_3'$ | $R_4'$ | $R_5'$ | Z |
|---|---|---|---|---|---|
| H | H | $OC_7H_7$ | $OC_7H_7$ | H | $(CH_2)_3-O-(3-C_2H_5C_6H_4)$ |
| H | $C_2H_5$ | H | $OC_7H_7$ | H | $(CH_2)_4-(2-n-C_3H_7C_6H_4)$ |
| H | H | Cl | $OCH_3$ | H | $(CH_2)_3-O-C_6H_5$ |
| H | $OC_7H_7$ | Br | H | H | $(CH_2)_3-C_6H_5$ |
| H | H | $OCH_3$ | $OC_7H_7$ | Br | $CH_2CH_2-C_6H_5$ |
| H | $CH_3$ | H | $CH_3$ | H | $(CH_2)_3-O-(3-HOC_6H_4)$ |
| H | H | H | $t-C_4H_9$ | H | $CH_2CH_2-O-(4-CH_3C_6H_4)$ |
| $n-C_4H_9$ | H | $SCH_3$ | H | H | $(CH_2)_3-O-(3-H_2NC_6H_4)$ |
| H | H | $SCH_3$ | H | H | $CH_2CH_2-C_6H_5$ |
| H | H | $SCH_3$ | $SCH_3$ | H | $(CH_2)_3-O-(2-H_2NC_6H_4)$ |
| H | $SC_7H_7$ | H | H | $SC_7H_7$ | $(CH_2)_4-C_6H_5$ |
| H | H | H | H | $SC_7H_7$ | $(CH)_2-(4-HOC_6H_4)$ |
| H | H | $SC_7H_7$ | $C_2H_5$ | H | $(CH_2)_3-(3-CH_3C_6H_4)$ |
| $CH_3$ | H | $OCH_3$ | $OCH_3$ | H | $CH_2CH_2-(2-HOOCC_6H_4)$ |
| H | H | Cl | $OCH_3$ | H | $CH_2-(4-H_2NC_6H_4)$ |
| $n-C_4H_9$ | $OCH_3$ | $-O-CH_2-O-$ | | H | $(CH_2)_3-(2-CH_3OC_6H_4)$ |
| H | H | H | H | H | $CH_2C_6H_5$ |
| H | H | $OCH_3$ | $OCH_3$ | H | $C_6H_5$ |
| H | H | H | OH | H | $4-H_2NC_6H_4$ |
| H | H | $SCH_3$ | H | H | $2-HOC_6H_4$ |
| H | H | $-OCH_2CH_2O-$ | | H | $4-HOOC-C_6H_4$ |
| H | H | Cl | $OC_7H_7$ | H | $2-CH_3OC_6H_4$ |
| H | H | $SC_7H_7$ | H | H | $4-n-C_4H_9OC_6H_4$ |
| H | $CH_3$ | $CH_3$ | H | H | $3-H_2NC_6H_4$ |
| H | H | $n-C_3H_7$ | H | H | $3-HOC_6H_4$ |
| H | H | $OCH_3$ | $OCH_3$ | H | $CH_2C_6H_5$ |
| H | H | $OCH_3$ | $OC_7H_7$ | H | $CH_2-(3-H_2NC_6H_4)$ |
| H | $OC_7H_7$ | Br | H | H | $CH_2-(2-C_2H_5OC_6H_4)$ |
| $C_6H_5$ | H | $SCH_3$ | H | H | $CH_2-(4-CH_3C_6H_4)$ |
| $C_6H_5$ | H | OH | $OCH_3$ | H | $CH_2-(3-HOOCC_6H_4)$ |
| H | H | SH | H | H | $C_6H_5$ |
| $C_2H_5$ | H | SH | OH | H | $2-CH_3OC_6H_4$ |
| H | H | F | OH | H | $3-H_2NC_6H_4$ |
| H | H | $OCH_3$ | OH | H | $CH_2CH_2-O-C_6H_5$ |
| $n-C_4H_9$ | H | H | $SOCH_3$ | H | $CH_2CH_2-O-C_6H_5$ |
| H | H | $SOC_7H_7$ | $C_2H_5$ | H | $CH_2CH_2-O-(3-H_2NC_6H_4)$ |
| H | H | H | H | $SOCH_3$ | $CH_2-(4-CH_3C_6H_4)$ |
| H | $SOC_7H_7$ | H | H | $SOC_7H_7$ | $CH_2-C_6H_5$ |
| H | $SOCH_3$ | H | H | H | $C_6H_5$ |
| $n-C_3H_7$ | H | $SOC_7H_7$ | H | H | $2-HOOCC_6H_4$ |
| H | H | H | H | H | $CH_2-(2-C_2H_5C_6H_4)$ |
| $C_6H_5$ | H | H | H | H | $4-CH_3C_6H_4$ |
| $CH_3$ | H | $OCH_3$ | $OCH_3$ | H | $4-t-C_4H_9C_6H_4$ |
| H | H | $OC_7H_7$ | $OCH_3$ | H | $3-C_2H_5C_6H_4$ |
| $CH_3$ | H | $-OCH_2CH_2O-$ | | H | $CH_2-(3-HOC_6H_4)$ |
| $n-C_4H_9$ | $OCH_3$ | $-O-CH_2-O-$ | | H | $4-n-C_4H_9OC_6H_4$ |
| $CH_3$ | H | Cl | Br | Cl | $CH_2C_6H_5$ |
| H | H | $SC_7H_7$ | H | H | $C_6H_5$ |
| H | H | $SCH_3$ | Cl | H | $CH_3$ |
| H | H | $SOCH_3$ | Cl | H | $CH_3$ |
| H | H | $SOCH_3$ | $SCH_3$ | H | $CH_3$ |
| $CH_3$ | H | $OCH_3$ | $OCH_3$ | H | $4-HOOCC_6H_4$ |
| H | H | $OC_7H_7$ | $OCH_3$ | H | $(CH_2)_2-(2-imidazolyl)$ |
| H | H | OH | $OCH_3$ | H | $(CH_2)_3-(2-imidazolyl)$ |
| H | H | $OCH_3$ | $OCH_3$ | H | $CH_2-(2-imidazolyl)$ |

EXAMPLE 12

Following the procedure of Example 2 but using the appropriate alkyl pyrimido[4,5-b]quinolin-4(3H)-one-2-carboxylate and the appropriate amines $H_2N2$ wherein Z is $-(alk)_m-(O)_n-W$ affords the compounds tabulated below.

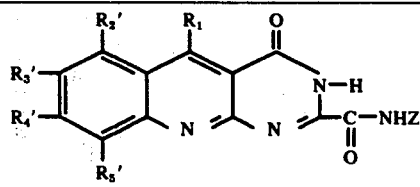

| $R_1$ | $R_2'$ | $R_3'$ | $R_4'$ | $R_5'$ | Z |
|---|---|---|---|---|---|
| H | H | H | H | H | $(CH_2)_4-O-C_6H_5$ |
| $C_6H_5$ | H | H | H | H | $(CH_2)_3-O-(2-pyridyl)$ |
| $CH_3$ | H | H | H | H | $(CH_2)_3-O-(4-H_2NC_6H_4)$ |

-continued

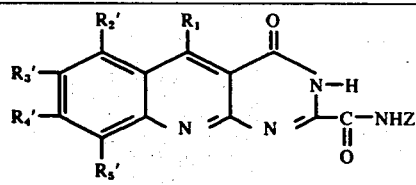

| R₁ | R₂' | R₃' | R₄' | R₅' | Z |
|---|---|---|---|---|---|
| n-C₄H₉ | H | H | H | H | (CH₂)₃—O—(2-CH₃C₆H₄) |
| H | H | H | H | H | (CH₂)₂—O—(4-imidazolyl) |
| H | H | OCH₃ | OCH₃ | H | (CH₂)₄—O—(2-pyridyl) |
| C₆H₅ | H | F | H | H | (CH₂)₂—O—(2-pyridyl) |
| H | H | OC₇H₇ | OCH₃ | H | (CH₂)₂—O—(2-imidazolyl) |
| H | H | OCH₃ | OC₇H₇ | H | (CH₂)₃—O—(4-pyridyl) |
| CH₃ | H | CH₃ | CH₃ | H | (CH₂)₄—O—(2-pyridyl) |
| H | H | Cl | Cl | H | (CH₂)₃—O—(4-pyridyl) |
| H | H | —OCH₂CH₂O— | | H | (CH₂)₂—O—(4-pyridyl) |
| H | H | —O—CH₂—O— | | H | (CH₂)₃—O—(2-pyridyl) |
| H | OCH₃ | —O—CH₂—O— | | H | (CH₂)₄—O—(3-pyridyl) |
| H | H | Br | H | Br | (CH₂)₂—O—(3-pyridyl) |
| H | H | OCH₃ | OCH₃ | OCH₃ | (CH₂)₃—O—(4-pyridyl) |
| C₆H₅ | H | SCH₃ | H | H | (CH₂)₂—O—(2-pyridyl) |
| H | C₂H₅ | OC₇H₇ | H | H | (CH₂)₂—O—(3-pyridyl) |
| H | H | OC₇H₇ | H | H | (CH₂)₃—O—(4-pyridyl) |
| n-C₄H₉ | C₂H₅ | OC₇H₇ | H | H | (CH₂)₂—O—(2-pyridyl) |
| H | H | H | SC₇H₇ | H | (CH₂)₄—O—(3-pyridyl) |
| H | H | F | OC₇H₇ | H | (CH₂)₂—O—(4-imidazolyl) |
| C₆H₅ | H | SOCH₃ | H | H | (CH₂)₂—O—(2-imidazolyl) |
| n-C₄H₉ | H | SOCH₃ | H | H | (CH₂)₂—O—(2-imidazolyl) |
| H | SOC₇H₇ | H | H | H | (CH₂)₂—O—(2-pyridyl) |
| H | SC₇H₇ | H | H | H | (CH₂)₂—O—(2-pyridyl) |
| H | H | OCH₃ | OC₇H₇ | H | (CH₂)₂—O—(4-imidazolyl) |
| H | H | OCH₃ | OH | H | (CH₂)₂—O—(2-pyridyl) |
| n-C₄H₉ | C₂H₅ | OH | H | H | (CH₂)₂—O—(4-imidazolyl) |
| H | H | OH | H | H | (CH₂)₃—O—(4-pyridyl) |
| H | SH | H | H | H | (CH₂)₂—O—(2-pyridyl) |
| H | H | OCH₃ | OCH₃ | H | (CH₂)₂—2—pyridyl |
| H | H | SCH₃ | Cl | H | (CH₂)₂—O—(2-pyridyl) |
| H | H | SOCH₃ | Cl | H | (CH₂)₂—O—(2-pyridyl) |
| H | H | SOCH₃ | SCH₃ | H | (CH₂)₂—O—(2-pyridyl) |
| CH₃ | H | OCH₃ | OCH₃ | H | 4-pyridyl |
| H | H | SCH₃ | H | H | 3-pyridyl |
| H | H | OC₇H₇ | OCH₃ | H | 2-pyridyl |
| C₆H₅ | H | —OCH₂CH₂O— | | H | 2-pyridyl |
| H | H | —O—CH₂—O— | | H | 2-pyridyl |
| n-C₄H₉ | H | SOCH₃ | H | H | 3-pyridyl |
| H | H | SC₇H₇ | C₂H₅ | H | 2-pyridyl |
| H | H | SOC₇H₇ | C₂H₅ | H | 4-imidazolyl |
| H | H | OCH₃ | OC₇H₇ | Br | 4-imidazolyl |
| C₂H₅ | OC₇H₇ | OCH₃ | H | H | 2-imidazolyl |
| C₆H₅ | H | H | H | H | CH₂—(2-imidazolyl) |
| H | H | —OCH₂CH₂O— | | H | (CH₂)₃—(2-pyridyl) |
| H | H | —O—CH₂—O— | | H | (CH₂)₂—(4-pyridyl) |
| H | Cl | H | H | H | (CH₂)₄—(2-pyridyl) |
| H | H | SCH₃ | SCH₃ | H | CH₂—(3-pyridyl) |
| H | H | SOCH₃ | SOCH₃ | H | CH₂—(3-pyridyl) |
| H | SC₇H₇ | H | H | SC₇H₇ | (CH₂)₂—(3-pyridyl) |
| H | SOC₇H₇ | H | H | SOC₇H₇ | (CH₂)₂—(3-pyridyl) |
| H | H | SC₇H₇ | H | H | (CH₂)₂—(4-imidazolyl) |
| H | H | Cl | OC₇H₇ | H | (CH₂)₂—(2-imidazolyl) |
| H | H | Cl | OH | H | (CH₂)₂—(2-imidazolyl) |
| CH₃ | H | CH₃ | CH₃ | H | CH₂—(2-imidazolyl) |
| H | H | OC₇H₇ | H | H | (CH₂)₄—O—(2-pyridyl) |
| H | H | OCH₃ | H | H | (CH₂)₃—O—(4-pyridyl) |
| H | H | OCH₃ | OCH₃ | H | (CH₂)₄—O—(2-pyridyl) |
| H | H | SCH₃ | H | H | (CH₂)₄—O—(3-pyridyl) |
| CH₃ | H | H | H | H | (CH₂)₃—O—(4-imidazolyl) |
| C₆H₅ | H | H | H | H | (CH₂)₄—O—(4-imidazolyl) |

EXAMPLE 13

The following compounds are prepared from appropriate amines and appropriate alkyl 3-substituted-pyrimido[4,5-b]quinolin-4(3H)-one-carboxylates according to the procedure of Example 5.

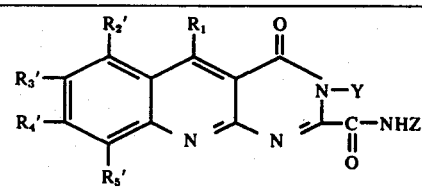

-continued

| R₁ | R₂' | R₃' | R₄' | R₅' | Z | Y |
|---|---|---|---|---|---|---|
| H | H | OCH₃ | OCH₃ | H | n-C₄H₉ | (CH₂)₂COOCH₃ |
| C₆H₅ | H | H | H | H | CH₃ | CH₂COOC₂H₅ |
| H | H | OCH₃ | H | OCH₃ | CH₃ | CH₂COO—n-C₃H₇ |
| H | H | OC₇H₇ | H | H | C₂H₅ | (CH₂)₂COOC₂H₅ |
| H | H | OC₇H₇ | OCH₃ | H | CH₃ | CH₂COOC₂H₅ |
| H | H | OCH₃ | OC₇H₇ | H | CH₃ | CH₂COOCH₃ |
| CH₃ | H | —OCH₂CH₂O— | | H | n-C₄H₉ | CH₂COOC₂H₅ |
| H | H | F | OC₇H₇ | H | CH₃ | CH₂COO—n-C₄H₉ |
| H | H | H | H | OC₇H₇ | CH₂CH₂OH | (CH₂)₂COO—n-C₄H₉ |
| CH₃ | H | —O—CH₂—O— | | H | CH₃ | (CH₂)₂COOC₂H₅ |
| H | H | —OCH₂CH₂O— | | H | (CH₂)₄OH | CH₂COOC₂H₅ |
| H | H | O—n-C₄H₉ | O—n-C₄H₉ | H | (CH₂)₃OH | (CH₂)₃COOCH |
| CH₃ | H | —OCH₂CH₂O— | | H | CH₂CH₂NH₂ | CH₂COOC₂H₅ |
| H | H | Br | H | Br | (CH₂)₄NH₂ | CH₂COOC₂H₅ |
| n-C₄H₉ | H | SCH₃ | H | H | n-C₃H₇ | CH₂COOC₂H₅ |
| H | H | SC₇H₇ | C₂H₅ | H | n-C₄H₉ | CH₂COOC₂H₅ |
| H | H | OCH₃ | OCH₃ | OCH₃ | C₆H₅ | (CH₂)₄COOC₂H₅ |
| H | H | F | OH | H | 4-H₂NC₆H₄ | CH₂COO—n-C₄H₉ |
| H | H | SCH₃ | H | H | 2-HOC₆H₄ | CH₂COOC₂H₅ |
| H | H | Cl | OC₇H₇ | H | 2-CH₃OC₆H₄ | CH₂COOC₂H₅ |
| H | CH₃ | H | CH₃ | H | 3-H₂NC₆H₄ | CH₂COOCH₃ |
| H | H | OCH₃ | OC₇H₇ | Br | CH₂C₆H₅ | CH₂COOC₂H₅ |
| H | OC₇H₇ | OCH₃ | OCH₃ | H | (CH₂)₃C₆H₅ | (CH₂)₄COOCH₃ |
| H | H | H | H | SC₇H₇ | (CH₂)₂—(4-HOC₆H₄) | (CH₂)₄COOC₂H₅ |
| H | OCH₃ | —O—CH₂—O— | | H | (CH₂)₃—O—(4-HOOCC₆H₄) | (CH₂)₂COOCH₃ |
| H | H | t-C₄H₉ | H | H | (CH₂)₂—O—(4-CH₃C₆H₄) | CH₂COOC₂H₅ |
| C₂H₅ | H | SH | H | H | 2-CH₃OC₆H₄ | CH₂COOCH₃ |
| H | H | OCH₃ | OH | H | (CH₂)₂—O—C₆H₅ | (CH₂)₃COOC₂H₅ |
| H | H | OC₂H₅ | O—n-C₄H₉ | H | C₆H₅ | (CH₂)₄COO—n-C₄H₉ |
| H | H | H | H | H | (CH₂)₃—O—4-H₂NC₆H₄ | CH₂COO—n-C₄H₉ |
| H | H | H | H | H | (CH₂)₂—O—4-imidazolyl | CH₂COOC₂H₅ |
| C₆H₅ | H | F | H | H | (CH₂)₂—O—(2-pyridyl) | CH₂COOCH₃ |
| H | H | OCH₃ | OCH₃ | H | (CH₂)₂—4-imidazolyl | (CH₂)₂COO—n-C₃H₇ |
| H | H | OCH₃ | OCH₃ | H | (CH₂)₂—O—(2-pyridyl) | CH₂COOCH₃ |
| H | H | OC₇H₇ | OCH₃ | H | (CH₂)₂—O—(3-pyridyl) | (CH₂)₂COOC₂H₅ |
| CH₃ | H | CH₃ | CH₃ | H | (CH₂)₄—O—(2-pyridyl) | (CH₂)₂COO—n-C₄H₉ |
| H | H | —OCH₂CH₂O— | | H | (CH₂)₂—O—(4-pyridyl) | CH₂COOC₂H₅ |
| C₆H₅ | H | SCH₃ | H | H | (CH₂)₂—O—2-pyridyl | CH₂COOC₂H₅ |
| n-C₄H₉ | H | SOCH₃ | H | H | (CH₂)₂—O—(2-pyridyl) | CH₂COOC₂H₅ |
| n-C₄H₉ | C₂H₅ | OH | H | H | (CH₂)₂—O—(2-imidazolyl) | CH₂COO—n-C₃H₇ |
| n-C₄H₉ | C₂H₅ | OC₇H₇ | H | H | (CH₂)₂—O—(2-imidazolyl) | CH₂COO—n-C₃H₇ |
| H | H | OCH₃ | OCH₃ | H | (CH₂)₂—(2-pyridyl) | CH₂COOC₂H₅ |
| H | H | —OCH₂CH₂O— | | H | (CH₂)₃—(2-pyridyl) | (CH₂)₄COOCH₃ |
| H | H | SCH₃ | SCH₃ | H | CH₂—(3-pyridyl) | CH₂COO—n-C₃H₇ |
| H | H | Cl | OC₇H₇ | H | (CH₂)₂—(2-imidazolyl) | (CH₂)₃COOCH |
| CH₃ | H | CH₃ | CH₃ | H | CH₂—(2-imidazolyl) | CH₂COOC₂H₅ |
| H | H | SCH₃ | H | H | 3-pyridyl | CH₂COOCH₃ |
| H | H | OCH₃ | OC₇H₇ | Br | 4-imidazolyl | CH₂COOC₂H₅ |
| H | H | —O—CH₂—O— | | H | 2-pyridyl | CH₂COOCH₃ |
| H | OC₇H₇ | OCH₃ | H | H | 2-imidazolyl | (CH₂)₃COOC₂H₅ |
| H | H | OCH₃ | OCH₃ | H | (CH₂)₄—O—(2-pyridyl) | CH₂COOC₂H₅ |
| C₆H₅ | H | F | H | H | (CH₂)₄—O—(3-pyridyl) | (CH₂)₃COOCH₃ |
| CH₃ | H | H | H | H | (CH₂)₃—O—(4-imidazolyl) | CH₂COOC₂H₅ |

EXAMPLE 14

The procedure of Example 8 is repeated but using as reactants the appropriate pyrimido[4,5-b]quinolin-4(3H)-ones and the appropriate bromoalkanoic acids to produce the following compounds:

| R₁ | R₂' | R₃' | R₄' | R₅' | Z | Y |
|---|---|---|---|---|---|---|
| H | H | H | H | H | (CH₂)₂—O—(3-H₂NC₆H₄) | CH₂COOH |
| H | H | OCH₃ | OCH₃ | H | (CH₂)₄—O—C₆H₅ | (CH₂)₄—COOH |
| C₆H₅ | H | OCH₃ | OCH₃ | H | CH₃ | CH₂COOH |
| H | H | H | H | H | (CH₂)₂—O—(2-pyridyl) | CH₂COOH |
| C₆H₅ | H | H | H | H | (CH₂)₂—O—(2-CH₃OC₆H₄) | (CH₂)₃COOH |
| CH₃ | H | H | H | H | (CH₂)₃—O—C₆H₅ | CH₂COOH |
| H | H | OC₇H₇ | OCH₃ | H | (CH₂)₂—O—(3-H₂NC₆H₄) | (CH₂)₄COOH |
| CH₃ | H | —O—CH₂CH₂—O— | | H | (CH₂)₃—O—(4-HOC₆H₄) | CH₂COOH |
| C₆H₅ | H | OCH₃ | OCH₃ | H | (CH₂)₄—O—4-HOOCC₆H₄) | (CH₂)₃COOH |
| H | H | Cl | OCH₃ | H | (CH₂)₃—O—C₆H₅ | CH₂COOH |
| H | H | —O—CH₂—O— | OCH₃ | H | (CH₂)₂—O—2-H₂NC₆H₄) | CH₂COOH |
| H | H | CH₃ | CH₃ | H | 3-H₂NC₆H₄ | (CH₂)₃COOH |
| H | H | OCH₃ | OCH₃ | H | C₆H₅ | CH₂COOH |
| H | H | Cl | OC₇H₇ | H | 2-CH₃OC₆H₄ | (CH₂)₄COOH |
| H | H | SCH₃ | SCH₃ | H | (CH₂)₃—O—2-H₂NC₆H₄) | CH₂COOH |
| n-C₄H₉ | OC₇H₇ | OCH₃ | OCH₃ | H | (CH₂)₂—O—C₆H₅ | (CH₂)₃COOH |
| CH₃ | H | OCH₃ | OCH₃ | H | 4-HOOCC₆H₄ | CH₂COOH |

| | | | | | | |
|---|---|---|---|---|---|---|
| H | H | SC₇H₇ | H | H | 4-n-C₄H₉OC₆H₄ | CH₂COOH |
| H | SOC₇H₇ | H | H | SOC₇H₇ | CH₂C₆H₅ | (CH₂)₄COOH |
| H | H | H | H | H | CH₂2-C₂H₅C₆H₄) | (CH₂)₃COOH |
| n-C₄H₉ | OCH₃ | —O—CH₂—O— | | H | 4-n-C₄H₉OC₆H₄ | CH₂COOH |
| CH₃ | H | OCH₃ | OCH₃ | H | 4-t-C₄H₉C₆H₄ | (CH₂)₂COOH |
| H | H | H | H | H | (CH₂)₂—O—(4-imidazolyl) | CH₂COOH |
| H | H | SOCH₃ | SOCH₃ | H | CH₂—(3-pyridyl) | (CH₂)₄COOH |
| H | H | Cl | OH | H | (CH₂)₂—2-imidazolyl) | (CH₂)₂COOH |
| n-C₄H₉ | H | SOCH₃ | H | H | (CH₂)₂—O—(2-imidazolyl) | CH₂COOH |
| H | H | —O—CH₂—O | | H | 2-pyridyl | CH₂COOH |
| n-C₄H₉ | H | SCH₃ | H | H | 3-pyridyl | (CH₂)₃COOH |
| CH₃ | H | OCH₃ | OCH₃ | H | 4-pyridyl | (CH₂)₄COOH |
| H | OC₇H₇ | OCH₃ | H | H | 2-imidazolyl | CH₂COOH |
| H | H | OCH₃ | OCH₃ | H | (CH₂)₄—O—(2-pyridyl) | CH₂COOH |
| H | H | SCH₃ | H | H | (CH₂)₄—O—(3-pyridyl) | (CH₂)₂COOH |
| CH₃ | H | H | H | H | (CH₂)₃—O—(4-imidazolyl) | CH₂COOH |
| C₂H₅ | H | H | H | H | (CH₂)₄—O—(4-imidazolyl) | (CH₂)₄COOH |

EXAMPLE 15

The sodium, potassium, calcium, magnesium, aluminum, ammonium, triethylamine, tri-n-butylamine, piperidine, triethanolamine, N-ethylpiperidine, piperidine, pyrrolidine, diethylaminoethylamine and N,N'-dibenzylethylenediamine salts of the compounds of this invention containing carboxy groups are prepared by reacting the compound with an equivalent amount of the appropriate metal hydroxide salt, ammonia or amine in water or ethanol. The salts are recovered by filtration if insoluble or by evaporation of the solvent if the salt is soluble therein.

EXAMPLE 16

Acid addition salts of the compounds described herein are prepared by reacting a compound of formula I with an equivalent amount of the appropriate acid in water, methanol or ethanol. The salts are recovered by filtration if insoluble or by evaporation of the solvent if soluble therein. In this manner the hydrochloride, acetate, propionate, butyrate, benzoate, citrate, maleate, fumarate, lactate, tartrate, sulfosalicylate and salicylate salts are prepared.

PREPARATION A

3-Aminophenoxyacetamide

A solution of 50% sodium hydride (5.76 g., 0.12 M), 3-hydroxyaniline (13.09 g., 0.12 M) and chloroacetamide (11.22 g., 0.12 M) is stirred at room temperature for 18 hours. The mixture is diluted with water to decompose residual sodium hydride and is then extracted with chloroform. The chloroform extract is dried (MgSO₄) and concentrated to an oil under reduced pressure. The addition of chloroform causes it to crystallize. Yield = 10.0g. (50%); m.p. 107°–111° C.

MS (molecular ion): 166.

NMR $\delta_{DMSO-d_6}^{TMS}$ : 4.31 (S,2,methylene); 5.06 (bd.S,2,amino); 6.03–6.38 (M,3,aromatic); 6.78–7.13 (M,1,aromatic); 7.38 (bd.S,2,amide).

The following compounds are prepared in like manner from appropriate W-OH and chloroacetamide, chloropropionamide or chlorobutyramide reactants:

| H₂N—CO—(CH₂)ₚ—O—W | | | |
|---|---|---|---|
| W | P | W | P |
| 3-NH₂ | 2 | 2-OH | 2 |
| 3-NH₂ | 3 | 3-OH | 3 |
| 2-NH₂ | 3 | 4-OH | 1 |
| 2-NH₂ | 2 | 4-OH | 2 |
| 4-NH₂ | 2 | 4-OH | 3 |
| 4-NH₂ | 3 | 4-COOH | 3 |

| H₂N—CO—(CH₂)ₚ—O—W | | | |
|---|---|---|---|
| W | P | W | P |
| H | 4 | 4-COOH | 2 |
| H | 2 | 3-COOH | 4 |
| H | 3 | 2-COOH | 2 |
| 4-CH₃ | 2 | 2-pyridyl | 2 |
| 3-CH₃ | 3 | 2-pyridyl | 3 |
| 3-CH₃ | 4 | 2-pyridyl | 4 |
| 4-n-C₄H₉ | 3 | 3-pyridyl | 2 |
| 3-C₂H₅ | 3 | 4-pyridyl | 3 |
| 2-n-C₃H₇ | 4 | 4-pyridyl | 2 |
| 2-OCH₃ | 1 | 3-pyridyl | 4 |
| 2-OCH₃ | 2 | 3-OCH₃ | 1 |
| 4-OCH₃ | 1 | 3-OC₂H₅ | 2 |
| 4-O-n-C₄H₉ | 2 | 4-CH₃OC₆H₄ | 1 |
| 3-H₂NC₆H₄ | 1 | 3-C₂H₅OC₆H₄ | 1 |
| 3-H₂NC₆H₄ | 2 | 4-n-C₄H₉C₆H₄ | 1 |
| 2-H₂NC₆H₄ | 1 | 2-HOC₆H₄ | 1 |
| 2-H₂NC₆H₄ | 2 | 3-HOC₆H₄ | 2 |
| 4-H₂NC₆H₄ | 1 | 4-HOC₆H₄ | 1 |
| H | 1 | 4-HOC₆H₄ | 2 |
| H | 2 | 4-HOC₆H₄ | 3 |
| H | 3 | 4-HOOCC₆H₄ | 1 |
| 4-CH₃C₆H₄ | 1 | 4-HOOCC₆H₄ | 2 |
| 3-CH₃C₆H₄ | 3 | 3-HOOCC₆H₄ | 3 |
| 3-CH₃C₆H₄ | 2 | 2-HOOCC₆H₄ | 1 |
| 4-n-C₄H₉C₆H₄ | 1 | 2-pyridyl | 1 |
| 3-C₂H₅C₆H₄ | 2 | 2-pyridyl | 2 |
| 2-n-C₃H₇C₆H₄ | 3 | 2-pyridyl | 3 |
| 2-CH₃OC₆H₄ | 1 | 3-pyridyl | 3 |
| 2-CH₃OC₆H₄ | 2 | 4-pyridyl | 2 |
| 4-n-C₄H₉OC₆H₄ | 1 | 4-pyridyl | 1 |
| 2-imidazolyl | 1 | 3-pyridyl | 1 |
| 4-imidazolyl | 1 | | |

PREPARATION B

2-(3-Aminophenoxy)ethylamine

A mixture of 3-aminophenoxyacetamide (10.0 g., 0.05 M), lithium aluminum hydride (6.8 g., 0.18 M) and ether (250 ml.) is refluxed under dry nitrogen for four days. It is then cooled to room temperature and water slowly added to decompose unreacted hydride. The precipitated salts are removed by filtration and the filtrate concentrated to an oil under reduced pressure. The crude oil is chromatographed on silica gel using 20% methanol/ethyl acetate as eluting agent. Concentration of appropriate fractions affords 4.83 g. (53%) of product as an oil. It is used without further purification.

In like manner, the remaining amides of Preparation A are converted to the corresponding amines.

PREPARATION C

2-(2-Pyridyloxy)ethylamine

A mixture of 2-hydroxyethylamine (6.1 g., 0.1 M) and 50% sodium hydride (4.8 g., 0.1 M) and dioxane (50 ml.), is refluxed for 30 minutes and is then cooled to room temperature. 2-Chloropyridine (11.36 g., 0.1 M) is added and the mixture refluxed for 18 hours. It is diluted with water (35 ml.) and then concentrated under reduced pressure. The residue is diluted with water and is then extracted with chloroform. The extract is dried ($Na_2SO_4$) and concentrated under vacuum to an oil. The oil is vacuum distilled to yield 11.5 g. (83%) of product; b.p. 70°–72° C. at 0.6 mm Hg.

NMR $\delta_{CF_3CO_2D}^{TMS}$ : 3.83 (bd.T,2); 4.90 (T,2,J = 5Hz); 7.43–7.83 (M,2, pyridine aromatic); 8.26–8.80 (M,2,pyridine aromatic).

Similarly, the following compounds are prepared by reaction of appropriate chloropyridines and bromoimidazoles with appropriate hydroxyalkylamines to produce compounds having the formula:

| —(alk)— | $H_2N$—(alk)—O—W W | —O—W —(alk)— | W |
|---|---|---|---|
| —(CH₂)₂— | 3-pyridyl | —(CH₂)₂— | 4-imidazolyl |
| —(CH₂)₂— | 4-pyridyl | —(CH₂)₃— | 4-imidazolyl |
| —(CH₂)₃— | 2-pyridyl | —(CH₂)₄— | 4-imidazolyl |
| —(CH₂)₃— | 4-pyridyl | —(CH₂)₂— | 2-imidazolyl |
| —(CH₂)₄— | 2-pyridyl | —(CH₂)₄— | 2-imidazolyl |
| —(CH₂)₄— | 3-pyridyl | | |

What is claimed is:

1. A compound of the formula

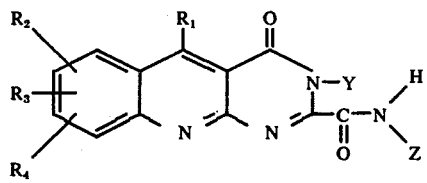

wherein
Z is selected from the group consisting of hydroxyalkyl having from two to four carbon atoms, aminoalkyl having from two to four carbon atoms; and —(alk)$_m$—(O)$_n$—W wherein
each of m and n is 0 or 1, provided that when n is 1, m is 1;
(alk) is alkylene having from one to four carbon atoms, provided that when n is 1, (alk) is alkylene having from two to four carbon atoms;
W is selected from the group consisting of pyridyl, imidazolyl and

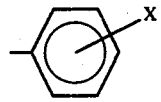

wherein X is selected from the group consisting of hydrogen, amino, carboxy, hydroxy, alkyl having from one to four carbon atoms and alkoxy having from one to four carbon atoms;
Y is selected from the group consisting of hydrogen, methyl, carboxyalkyl having from one to four carbon atoms in the alkyl group and carbalkoxyalkyl having from one to four carbon atoms in each of the alkyl and alkoxy groups;

$R_1$ is selected from the group consisting of hyrogen, alkyl having from one to four carbon atoms and phenyl;
each of $R_2$, $R_3$ and $R_4$ when taken separately is selected from the group consisting of hydrogen, alkyl having from one to four carbon atoms, alkoxy having from one to four carbon atoms, halo, hydroxy, benzyloxy, benzoyloxy, alkanoyloxy having from one to four carbon atoms, thiol, methylthio, methylsulfinyl, benzylthio and benzylsulfinyl;
with the proviso that no more than two of $R_2$, $R_3$ and $R_4$ are branched alkyl or alkoxy, and when two of $R_2$, $R_3$ and $R_4$ are branched chain alkyl or alkoxy, said groups are located on non-adjacent carbon atoms;
$R_2$ and $R_3$ or $R_3$ and $R_4$ when taken together are alkylenedioxy and are selected from the group consisting of methylenedioxy and ethylenedioxy;
with the proviso that only one of said pairs is alkylenedioxy; and
the pharmaceutically acceptable acid addition salts thereof, and the pharmaceutically acceptable cationic salts of those compounds wherein W is carboxyphenyl or Y is carboxyalkyl.

2. A compound according to claim 1 wherein each of $R_1$, $R_2$, $R_3$, $R_4$ and Y is hydrogen, and Z is —(alk)$_m$—(O)$_n$—W.

3. A compound according to claim 2 wherein W is

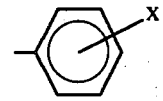

and each of m and n is 1.

4. The compound according to claim 3 wherein X is hydrogen and —(alk)— is —CH₂CH₂—.

5. The compound according to claim 3 wherein X is 3-amino and —(alk)— is —(CH₂CH₂—.

6. A compound according to claim 1 wherein each of $R_1$, $R_2$ and Y is hydrogen; each of $R_3$ and $R_4$ is alkoxy; and Z is —(alk)$_m$—(O)$_n$—W.

7. A compound according to claim 6 wherein each of m and n is 1; —(alk)— is —CH₂CH₂—; each of $R_3$ and $R_4$ is methoxy; and W is

8. The compound according to claim 7 wherein X is hydrogen.

9. The compound according to claim 7 wherein X is 3-amino.

10. A compound according to claim 6 wherein W is 2-pyridyl.

11. The compound according to claim 10 wherein each of $R_3$ and $R_4$ is methoxy; each of m and n is 1; and —(alk)— is —CH₂CH₂—.

12. The compound according to claim 1 wherein each of $R_1$, $R_2$ and Y is hydrogen; each of $R_3$ and $R_4$ is methoxy; and Z is hydroxyethyl.

13. A compound according to claim 1 wherein each of $R_1$ and $R_2$ is hydrogen; each of $R_3$ and $R_4$ is alkoxy; Y is carbalkoxyalkyl, and Z is —(alk)$_m$—(O)$_n$—W.

14. The compound according to claim 13 wherein each of $R_3$ and $R_4$ is methoxy; Y is carbethoxymethyl; each of m and n is 1 and W is 2-pyridyl.

15. A compound according to claim 6 wherein W is 2-pyridyl.

16. A method for the control of peptic ulcers in animals in need of said treatment which comprises administering, by either the intraperitoneal or oral route to the animals an antipeptic ulcer amount of a compound having the formula

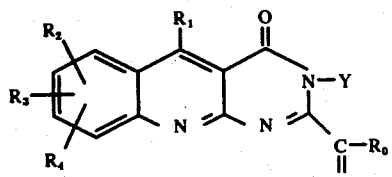

wherein
$R_0$ is selected from the group consisting of alkoxy having from one to four carbon atoms, and NHZ wherein Z is selected from the group consisting of hydrogen, hydroxyalkyl having from two to four carbon atoms, aminoalkyl having from two to four carbon atoms; alkyl having from one to four carbon atoms and:

$$-(alk)_m-(O)_n-W$$

wherein
each of m and n is 0 or 1, provided that when n is 1, m is 1;
(alk) is alkylene having from one to four carbon atoms, with the proviso that when n is 1, (alk) is alkylene having from two to four carbon atoms;
W is selected from the group consisting of pyridyl, imidazolyl and

wherein X is selected from the group consisting of hydrogen, amino, carboxy, hydroxy, alkyl having from one to four carbon atoms and alkoxy having from one to four carbon atoms;
Y is selected from the group consisting of hydrogen, methyl, carboxyalkyl having from one to four carbon atoms in the alkyl group and carboxyalkyl having from one to four carbon atoms in each of the alkyl and alkoxy groups;
$R_1$ is selected from the group consisting of hydrogen, alkyl having from one to four carbon atoms and phenyl;

each of $R_2$, $R_3$ and $R_4$ when taken separately is selected from the group consisting of hydrogen, alkyl having from one to four carbon atoms, alkoxy having from one to four carbon atoms, halo, hydroxy, benzyloxy, benzoyloxy, alkanoyloxy having from one to four carbon atoms, thiol, methylthio, methylsulfinyl, benzylthio and benzylsulfinyl;
with the proviso that no more than two of $R_2$, $R_3$ and $R_4$ are branched alkyl or alkoxy, and when two of $R_2$, $R_3$ and $R_4$ are branched chain alkyl or alkoxy, said groups are located on non-adjacent carbon atoms;
$R_2$ and $R_3$ or $R_3$ and $R_4$ when taken together are alkylenedioxy and are selected from the group consisting of methylenedioxy and ethylenedioxy;
with the proviso that only one of said pairs is alkylenedioxy; and
the pharmaceutically acceptable acid addition salts thereof, and the pharmaceutically acceptable cationic salts of those compounds wherein W is carboxyphenyl or Y is carboxyalkyl.

17. The method of claim 16 wherein each of $R_1$, $R_2$, $R_3$, $R_4$ and Y is hydrogen; and Z is $-(alk)_m-(O)_n-W$.

18. The method of claim 17 wherein each of m and n is 1 and W is

19. The method of claim 18 wherein X is hydrogen and $-(alk)-$ is $-CH_2CH_2-$.

20. The method of claim 17 wherein X is 3-amino and $-(alk)-$ is $-CH_2CH_2-$.

21. The method of claim 16 wherein each of $R_1$, $R_2$ and Y is hydrogen; each of $R_3$ and $R_4$ is alkoxy; and Z is $-(alk)_m-(O)_n-W$.

22. The method of claim 21 wherein each of m and n is 1; $-(alk)-$ is $-CH_2CH_2-$; each of $R_3$ and $R_4$ is methoxy; and W is

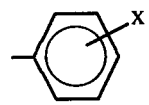

23. The method of claim 22 wherein X is 3-amino.

24. The method of claim 21 wherein each of m and n is 1; $-(alk)-$ is $-CH_2CH_2-$; each of $R_3$ and $R_4$ is methoxy; and W is 2-pyridyl.

25. The method of claim 16 wherein each of $R_1$, $R_2$ and Y is hydrogen; each of $R_3$ and $R_4$ is methoxy; and Z is hydroxyethyl.

26. The method of claim 16 wherein each of $R_1$, $R_2$ and Y is hydrogen; each of $R_3$ and $R_4$ is methoxy and $R_0$ is alkoxy.

27. The method of claim 26 wherein $R_0$ is ethoxy.

* * * * *